United States Patent
Freebeck et al.

(10) Patent No.: US 7,809,590 B2
(45) Date of Patent: Oct. 5, 2010

(54) HEALTHCARE CHARGE CAPTURE AND INFORMATION DELIVERY SYSTEM AND METHOD

(75) Inventors: Peter Freebeck, La Grange, IL (US); Jack Thomas, La Grange, IL (US)

(73) Assignee: ASN, Inc., Westmont, IL (US)

( * ) Notice: Subject to any disclaimer, the term of this patent is extended or adjusted under 35 U.S.C. 154(b) by 755 days.

(21) Appl. No.: 11/775,603

(22) Filed: Jul. 10, 2007

(65) Prior Publication Data

US 2009/0018861 A1 Jan. 15, 2009

(51) Int. Cl.
*G06Q 10/00* (2006.01)
*G06Q 50/00* (2006.01)
*G06Q 40/00* (2006.01)
*A61B 5/00* (2006.01)
*G06F 19/00* (2006.01)

(52) U.S. Cl. .................................. 705/4; 705/2; 705/3
(58) Field of Classification Search ...................... 705/2, 705/3, 4
See application file for complete search history.

(56) References Cited

U.S. PATENT DOCUMENTS

| | | | | |
|---|---|---|---|---|
| 4,491,725 | A | * | 1/1985 | Pritchard ........................ 705/2 |
| 5,845,253 | A | * | 12/1998 | Rensimer et al. ............... 705/2 |
| 6,154,726 | A | * | 11/2000 | Rensimer et al. ............... 705/2 |
| 7,110,955 | B1 | * | 9/2006 | Barhnart et al. ................. 705/3 |
| 2006/0047568 | A1 | * | 3/2006 | Eisenberg et al. .............. 705/14 |
| 2006/0047572 | A1 | * | 3/2006 | Moore et al. ................... 705/14 |

OTHER PUBLICATIONS

Health and Medical information produced by Doctors—Medicinenet, Jun. 2007, http://web.archive.org/web/20070630050439/www.medicinenet.com/script/main/hp.asp.*

Hau et al., "Patientkeeper Awarded U.S. Patent for Automating Physician Charge Capture Through Innovative Software Technology," Bergstrom, Scott, PatientKeeper®, Inc., Oct. 16, 2006, Internet article, 2 pp.

Healthcare IT News, "Practice Fusion Offers Free EMRs to docs, paid for by ads," by Diana Manos, Mar. 19, 2007, Internet article, 1 pg.

Healthcare IT News, "Buyers Guide: Handhelds," Sep. 1, 2005, Internet article, 7 pp.

Practice Fusion, On Demand Claims Management Service™, Internet article, 2007, 1 pg.

Vara, Vauhini, "Companies Tolerate Ads to Get Free Software," *The Wall Street Journal Online*, Mar. 27, 2001, 5 pp.

* cited by examiner

*Primary Examiner*—Gerald J. O'Connor
*Assistant Examiner*—Amber Altschul
(74) *Attorney, Agent, or Firm*—Brinks Hofer Gilson & Lione

(57) ABSTRACT

A provider-patient encounter device delivers medical information and services by receiving content from context sponsors, linking the content to service codes and presenting the content to providers. The service codes represent medical procedure codes and medical diagnosis codes. Each service code includes a provider demographic code, a service priority code, and a supplemental service code. The provider-patient encounter device presents a selectable list of service codes and presents content from a context sponsor assigned to a service code when the provider selects the service code from the selectable list of service codes.

21 Claims, 16 Drawing Sheets

| LynxIT Solution | | 412 | Date | 236 | Time | 238 |
|---|---|---|---|---|---|---|
| Service Code Selector | | 602 | Patient ID | | | 234 |

| | | | | | |
|---|---|---|---|---|---|
| Add 616 | Service Code-1 | 604 | ∧ | Context Sponsor (CS)-2 Name | 622 |
| | Service Code-2 | 606 | = | CS Service Code-2 Name | 624 |
| Delete 618 | Service Code-3 | 608 | | CS Service Code-2 Content | 626 |
| | Service Code-4 | 610 | | | |
| | Service Code-5 | 612 | ∨ | | |

614

| Service Code-2 Description | 620 |
|---|---|

| Command Bar | 410 |
|---|---|

| Supplemental Service Code (SSC) Selector | 802 | Patient ID | 234 |

| SSC-1 | 804 |
| SSC-2 | 806 |
| SSC-3 | 808 |
| SSC-4 | 810 |
| SSC-5 | 812 |
| SSC-6 | 814 |
| SSC-8 | 816 |

SSC Content Delivery Method 222

| Patient Physical Address | 818 |
| Provider Location | 820 |
| Electronic Messaging to Patient | 822 |
| Patient Voice Messaging | 824 |

Command Bar 410

| Browser Interface | | 1102 | Date | 236 | Time | 238 |
|---|---|---|---|---|---|---|
| Address Bar | 1106 | Service Code Time Slot – Schedule Location | | | | 1104 |
| Service Code Pull-Down List | | 1118 | Service Code-7 | | | 1108 |

SCTS-1 Schedule   1110
- SCTS Time Period-1: Date-1 | Start Time-1 | End Time-1
- SCTS GEO-1   324
- SCTS Priority-1

SCTS-2 Schedule   1112
- SCTS Time Period-1: Date-1 | Start Time-1 | End Time-1
- SCTS GEO-1
- SCTS Priority-1

SCTS-3 Schedule   1114
- SCTS Time Period-4: Date-2 | Start Time-4 | End Time-4
- SCTS GEO-1
- SCTS Priority-1

SCTS-4 Schedule   1116
- SCTS Time Period-3: Date-2 | Start Time-3 | End Time-3
- SCTS GEO-1
- SCTS Priority-1

| Command Bar | SCTS Utilization Statistics | 1120 |
|---|---|---|

| Browser Interface | | 1102 | Date | 236 | Time | 238 |
|---|---|---|---|---|---|---|
| Address Bar | 1106 | Service Code Time Slot - Context Sponsor (CS) Assignments | | | | 1202 |
| CS ID-1 | 328 | Service Code Pull-Down List | 1118 | Service Code-5 | | 1224 |

- SCTS-1 Schedule   1214
  - Status-1   1230 | Rate-1 | Rank-1   1232 | Assignment-1   1204

- SCTS-2 Schedule   1216
  - Status-2 | Rate-2 | Rank-2 | Assignment-2   1206

- SCTS-3 Schedule   1218
  - Status-3 | Rate-3 | Rank-3 | Assignment-3   1208

- SCTS-4 Schedule   1220
  - Status-4 | Rate-4 | Rank-4 | Assignment-4   1210

- SCTS-5 Schedule   1222
  - Status-5 | Rate-5 | Rank-5 | Assignment-5   1212

| Command Bar | Clear | 1226 | Submit | 1228 | |

| Browser Interface | 1102 | Date | 236 | Time | 238 |
| Address Bar | 1102 | Context Sponsor - Content Management Location | | | 1304 |
| CS ID-1 | 328 | Service Code Pull-Down List | 1118 | Service Code-7 | 1302 |

Context Sponsor (CS) Name     214

CS Service Code Name     216

CS Service Code Content     218

- CS Service Code Text Content     260
- CS Service Code Video Content     262
- CS Service Code Audio Content     264
- CS Service Code Other Sensory Content     1306

| Command Bar | Clear | Submit | |

| LynxIT Solution | | 412 | Date | 236 | Time | 238 |
|---|---|---|---|---|---|---|
| Patient ID : | | 234 | 987654321 | | | |

| Service Code Link | 1416 | Service Code-2 | 1402 | Service Code Type-2 | 1414 |

SC Type - Medical Diagnosis

| | Available SC | 1418 | ∧ |
|---|---|---|---|
| Add | Service Code-1 | 1410 | = |
| | Service Code-9 | 1404 | |
| Delete | Service Code-3 | 1412 | ∨ |

| Linked SC | 1420 | ∧ |
|---|---|---|
| Service Code-4 | 1404 | = |
| Service Code-9 | 1406 | |
| Service Code-8 | 1408 | ∨ |

1422

Service Code-9 Description   1424

Command Bar

| LynxIT Solution | 412 | Date | 236 | Time | 238 |
| Patient Profile Interface | 1502 | Patient ID | 234 | 987654321 |

254

- Medical Record No. — 1234567
- Last Name : Patient Last Name
- First Name : Patient First Name — MI :
- Birth Date : MM/DD/YYYY — M/F
- Loc : Inpatient/Outpatient — Rm : 1234
- Default SSC Content – Preferred Delivery Method — 1506 — Electronic Messaging
- Referring MD : Referring MD Name

1504

```
123 1 2 3 4 5 6 7 8 9 0 - = ←
Tab q w e r t y u i o p [ ]
CAP a s d f g h j k l ; '
Shift z x c v b n m , . / ↵
Ctl áü ` \            ↓ ↑ ← →
```

Command Bar

Figure 15

HEALTHCARE CHARGE CAPTURE AND INFORMATION DELIVERY SYSTEM AND METHOD

BACKGROUND OF THE INVENTION

1. Technical Field

This disclosure concerns capturing charges for medical diagnosis and procedures, and presenting healthcare information, products and services to providers and patients. In particular, this disclosure relates to an efficient and economical approach to healthcare advertising and reporting utilization statistics to advertisers for content presented, selected or requested by a provider.

2. Background Information

Healthcare service providers (e.g., physicians, psychologists, nurse practitioners, physician assistants, therapists, and provider billing) employ a process known as charge capture that uses medical diagnosis and procedure codes (e.g., ICD-9 and CPT codes published by the American Medical Association AMA) to generate claims for reimbursements from payers (e.g., an insurance company, and Medicare) resulting from provider-patient encounters (e.g., patient consultation with a provider for treatment). Many healthcare service providers (providers) use handwritten charge cards or sheets to capture (charge capture) the medical diagnosis and procedures identified during the provider-patient encounter. Manual charge capture often leads to under coding, and over coding medical diagnosis and procedure codes resulting in payers rejecting claims. Manual charge capture also leads to improper and unidentified linking of procedure codes with diagnosis codes. Manual charge capture methods further lead to inefficiencies and inaccuracies that result in loss of revenue (e.g., failing to realize full reimbursements for services), as well as delayed reimbursements to providers.

Manual charge capture often includes the inefficient and cumbersome delivery of paper charge sheets to billing departments, the difficult task of deciphering the handwriting of providers, and inaccurate healthcare documentation jeopardizing the quality of healthcare delivered to patients. Outdated charge capture methods typically interface with outdated billing systems and methods that do not provide an efficient way to confirm that provider claims have met all the requirements of payers. The significant upfront financial outlay required to implement an automated charge capture system deters many providers from migrating away from manual charge capture, even though automated charge capture systems may enable a provider to realize a return on investment quickly.

The healthcare industry continues to realize the rapid development of medical products and services that providers may use in the treatment of patients. However, challenges exist for the healthcare industry to realize effective and economically efficient methods of delivering information to providers regarding medical products and services related to medical diagnosis and procedures identified during provider-patient encounters. Healthcare advertisers (e.g., medical suppliers, drug companies, medical equipment, and assisted living services) continually pursue opportunities to present information regarding their products and services to providers. However, advertisers require a method of advertising that enables advertisers to measure the effectiveness of their advertising investment.

Manual charge capture and the inability of providers to efficiently realize products and services relevant to medical diagnosis and procedures identified during provider-patient encounters prevent providers from delivering the most timely and greatest quality of healthcare to patients. Providers that use manual charge capture methods miss the opportunity to effortlessly review the latest available information regarding relevant products and services before prescribing treatment for patients. Providers and healthcare advertisers have a common need for a system and method that presents timely information regarding available products and services that facilitates delivery of the greatest quality of healthcare to patients.

A need has long existed for a system and method to effectively and economically implement electronic charge capture and deliver healthcare advertising to providers and patients.

SUMMARY

The LynxIT system configuration provides a method for delivering medical information and services. The LynxIT system configuration receives content from context sponsors (e.g., healthcare advertisers) and links the content from the context sponsors to service codes that represent medical procedure codes and medical diagnosis codes. Each service code may include a provider demographic code, a service priority code, and a supplemental service code. The LynxIT system (e.g., provider-patient encounter system) presents content from a context sponsor assigned to a service code when the provider selects the service code from a list of selectable service codes presented to the provider on a provider-patient encounter device (e.g., a handheld device). The LynxIT system configuration includes a machine readable medium that includes user interface logic to receive content from context sponsors and assign content from the context sponsors to service codes. The user interface logic may present the service codes in a service code selectable list to the provider and presents content from a context sponsor assigned to a service code when the provider selects the service code from the list of service codes. The user interface logic may request context sponsors forward supplemental service code content associated with a supplemental service code to the provider. The user interface logic may also forward supplemental service code content to a patient. The LynxIT system configuration includes generation logic to generate billing information (e.g., a charge to a payer) based on a service code selected by the provider.

The LynxIT system configuration includes a memory that stores the user interface logic that presents a service code time slot to context sponsors. The service code time slot identifies a time period during which content from a context sponsor may be presented to a provider for a corresponding service code when the provider selects the service code. The user interface logic receives a request from a context sponsor for a service code time slot and content from the context sponsor corresponding to the service code. The LynxIT system configuration includes definition logic that assigns a service code and service code time slot to a context sponsor. The LynxIT system configuration definition logic may also assign a supplemental service code associated with a corresponding service code to a context sponsor. The same or different context sponsors may be assigned a service code and supplemental service code corresponding to the service code. The LynxIT system configuration also includes a provider database, and a processor coupled to the memory and the database to execute the user interface logic, definition logic and generation logic.

Other systems, methods, and features of the invention will be, or will become, apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The disclosure can be better understood with reference to the following drawings and description. The components in the figures are not necessarily to scale, emphasis instead being placed upon illustrating the principles of the invention. Moreover, in the figures, like referenced numerals designate corresponding parts or elements throughout the different views.

FIG. 6 shows a service code selector interface.

FIG. 8 illustrates a supplemental service code selector interface.

FIG. 11 illustrates a service code time slot (SCTS) schedule viewer.

FIG. 12 illustrates a service code time slot (SCTS) context sponsor assignment site.

FIG. 13 illustrates a context sponsor content input site.

FIG. 14 illustrates a service code link interface.

FIG. 15 illustrates a provider-patient encounter device patient profile interface.

DETAILED DESCRIPTION

Figure 1:
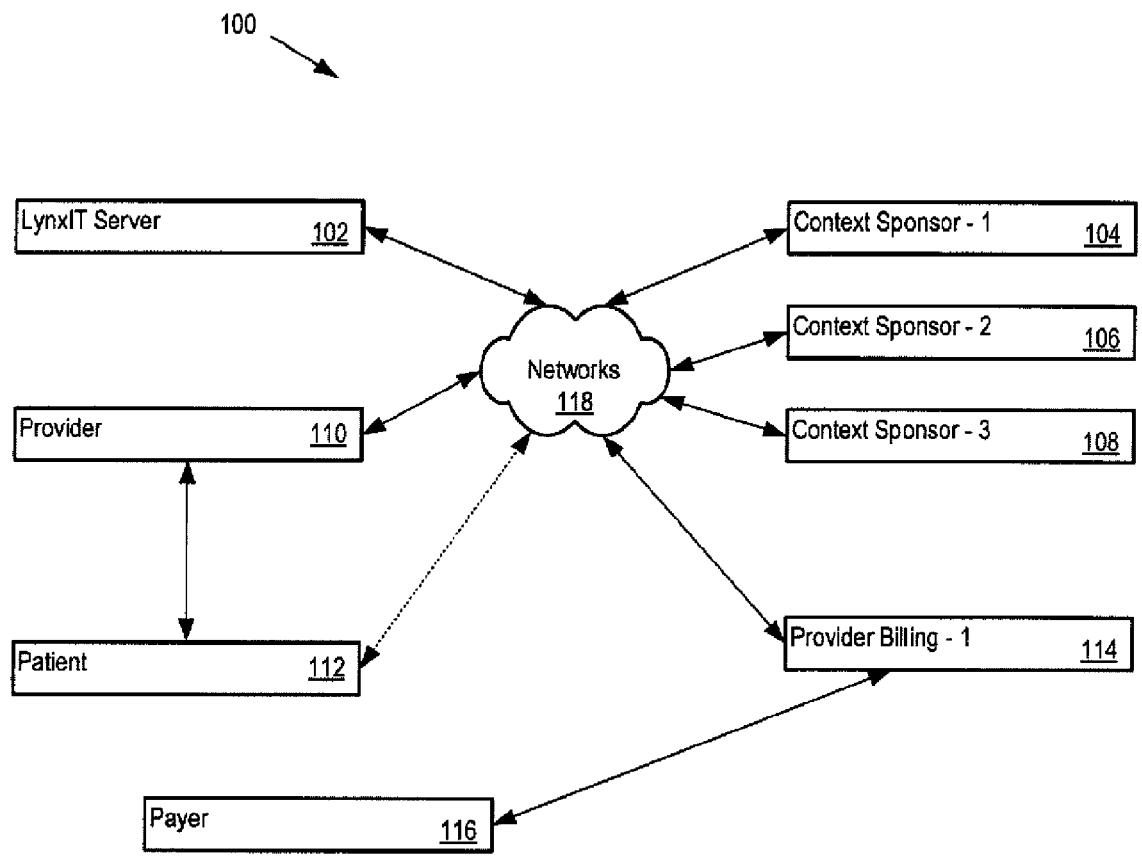
FIG. 1 shows a LynxIT system configuration.

The LynxIT system configuration may include a provider-patient encounter device that delivers electronic charge capture capabilities to providers, and enables advertisers to present their products and services to providers effectively and economically. The LynxIT system configuration may also include a LynxIT server that communicates with context sponsors to receive healthcare advertising (e.g., context sponsor content) regarding the effectiveness of a particular drug, medical device, or medical service. The LynxIT server may deliver context sponsor content to a provider, who in turn may deliver the content to a patient to assist the patient in understanding their medical condition. In one implementation, only the provider has the authority to determine whether to deliver content received from the LynxIT system configuration to a patient. In an alternative implementation, the patient may authorize the provider to deliver content to the patient electronically (e.g., electronic messaging). The LynxIT system configuration may enable the provider to automatically generate a charge for a provider-patient encounter (e.g., diagnosing the condition of a patient, and prescribing a medical procedure for treatment). The LynxIT system configuration 100 may also electronically forward the charge automatically to provider billing.

The LynxIT server may present service code time slots (e.g., time periods when the provider-patient encounter device may present context sponsor content to a provider) to context sponsors, and enable context sponsors to request service code time slots. A LynxIT administrator may evaluate requests for service code time slots received from a context sponsor for a service code time slot schedule for a particular service code to determine service code time slot assignments for context sponsors. The LynxIT server administrator may deliver approved context sponsor content to the provider-patient encounter device. The provider-patient encounter device may present the context sponsor content to the provider during the service code time slot, and operate to collect and report context sponsor utilization statistics to users authorized by the LynxIT server.

In one implementation, the LynxIT server assigns a context sponsor a default service code (e.g., a provider demographic code indicating a medical specialty) that directs the provider-patient encounter device to present the context sponsor content in a default context content area (e.g., login screen of the provider-patient encounter device) without requiring the provider to invoke a service code. In the above implementation, the provider-patient encounter device and the LynxIT server may operate to record each occasion when the context sponsor default context content area presents the assigned context sponsor content to the provider.

A provider may access use of the provider-patient encounter device by entering a PIN number, and identify their provider demographics (e.g., medical specialty). Similarly, the provider may identify their provider GEO sensitivity (e.g., a state, region or global code, zip code and radius designation) indicating whether to deliver context sponsor content to the provider specific to a geographical region. During a provider-patient encounter the provider may establish, and confirm with the patient a method of delivery of context sponsored content. During the provider-patient encounter the provider may also select a service code in the course of providing treatment to the patient. The provider-patient encounter device may determine the context sponsor content to present to the provider based on the service code selected by provider, and in the event the provider requests additional information, the LynxIT server may present the additional content to the provider. The LynxIT server may also deliver the additional content to a provider controlled information delivery system. The provider may deliver the additional content to the patient using the delivery method established by the patient and provider.

The provider-patient encounter device and the LynxIT server may collect context sponsor utilization statistics each time the provider-patient encounter device presents context sponsor content to a provider. The LynxIT server may use the context sponsor utilization statistics to inform a context sponsor regarding the effectiveness of their advertising investment, evaluate the rates offered to context sponsors for service code time slots, and operate to analyze the effectiveness of service code time slots assignments to context sponsors. The LynxIT system configuration and provider-patient encounter device enable providers and healthcare advertisers to address a common need for a system and method that presents timely healthcare information regarding available products, services, and information that facilitates delivery of the greatest quality of healthcare to patients.

Although specific components of the LynxIT system configuration will be described, methods, systems, and articles of manufacture consistent with the LynxIT system configuration may include additional or different components. For example, a processor may be implemented as a microprocessor, microcontroller, application specific integrated circuit (ASIC), discrete logic, or a combination of other type of circuits or logic. Similarly, memories may be DRAM, SRAM, Flash or any other type of memory. Logic that implements the processing and programs described below may be stored (e.g., as computer executable instructions) on a computer readable medium such as an optical or magnetic disk or other memory. Alternatively or additionally, the logic may be realized in an electromagnetic or optical signal that may be transmitted between entities. An example of such a signal is a physical layer Ethernet signal bearing TCP/IP packets that include program source code or executable programs. Flags, data, databases, tables, and other data structures may be separately stored and managed, may be incorporated into a single memory or database, may be distributed, or may be logically and physically organized in many different ways. Programs may be parts of a single program, separate programs, or distributed across several memories and processors. Furthermore, the programs, or any portion of the programs, may instead be implemented in hardware.

FIG. 1 shows a LynxIT system configuration 100. The LynxIT system configuration 100 may include various components, including: a LynxIT server 102, context sponsors (e.g., context sponsor-1 104, context sponsor-2 106, and context sponsor-3 108), a provider 110, a patient 112, provider billing 114, and a payer 116. The LynxIT system configuration 100 may use a network 118 (e.g., the "Internet") to communicate between the various components. In one implementation, the LynxIT server 102 communicates through the network 118 with the context sponsors to receive context sponsor content regarding the effectiveness of a particular drug, medical device, or medical service. The LynxIT server 102 may deliver context sponsor content to provider 110. Provider 110 may deliver the content to patient 112 to assist patient 112 in understanding their medical condition, and potentially affect the outcome of their treatment. In one implementation, only provider 110 has the authority to determine whether to deliver information received from the LynxIT system configuration 100 to patient 112. In an alternative implementation, patient 112 may authorize provider 110 to deliver content to patient 112 through the network 118. The LynxIT system configuration 100 may enable provider 110 to automatically generate a charge for a provider-patient encounter (e.g., diagnosing the condition of a patient, and prescribing a medical procedure for treatment). The LynxIT system configuration 100 may also enable provider 110 to electronically forward the charge to provider billing 114.

Figure 2:
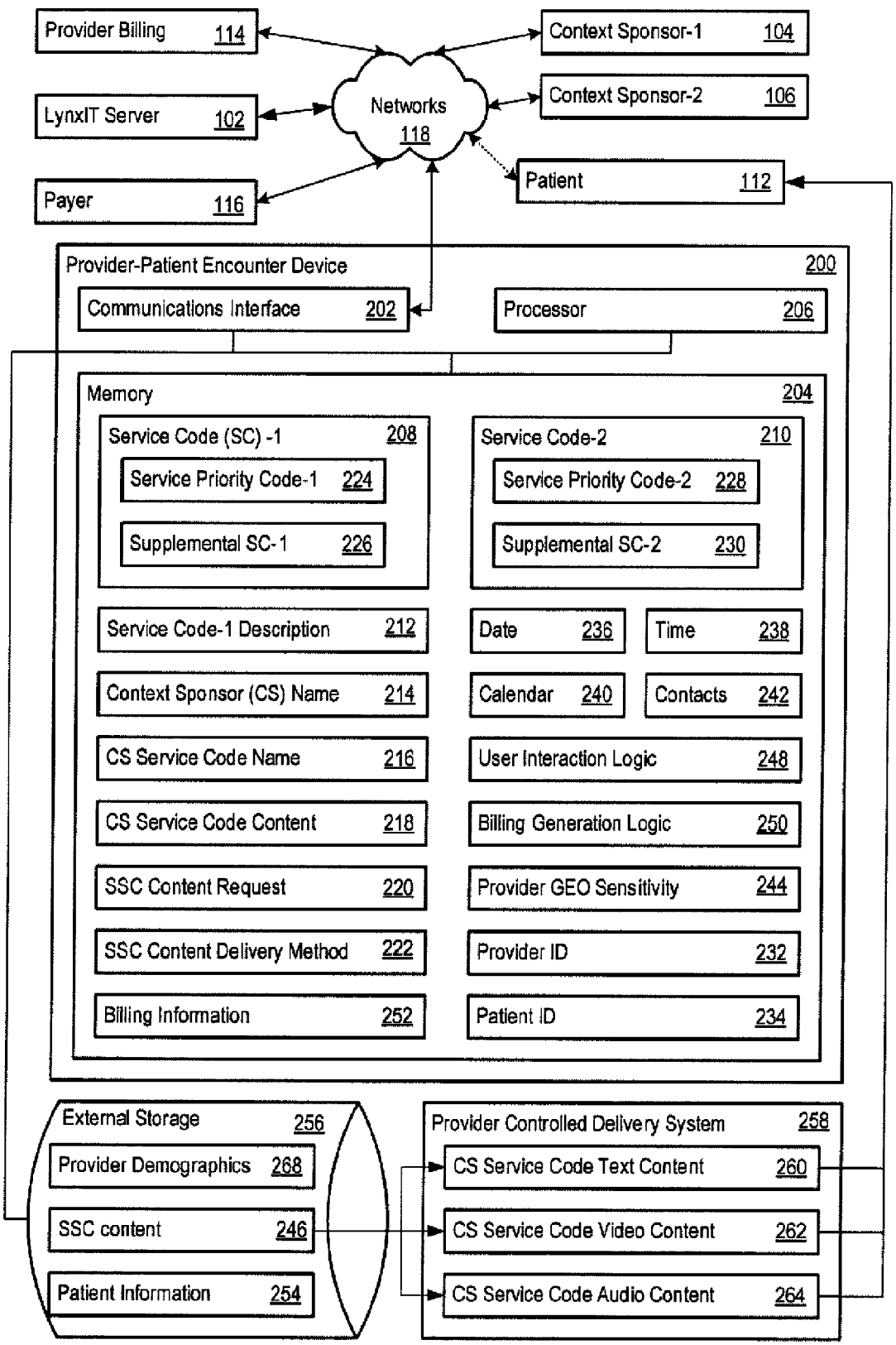
FIG. 2 illustrates a provider-patient encounter device.

FIG. 2 illustrates a provider-patient encounter device 200. The provider-patient encounter device 200 may include: a communication interface 202, a memory 204, and a processor 206. In one implementation, the provider-patient encounter device 200 may be implemented as an application executed on a system that includes a communication interface 202, memory 204, and processor 206. In another implementation, the communication interface 202 enables the exchange of information between the LynxIT server 102, the context sponsors (e.g., context sponsor-1 104), and provider 110 via the provider-patient encounter device 200. The exchange of information may include content from the context sponsors (e.g., context sponsor-1 104) delivered to provider 110 by the LynxIT server 102 via the provider-patient encounter device 200. In one implementation, the provider-patient encounter device 200 may receive content through the communication interface directly from a context sponsor (e.g., context sponsor-2 106). The communication interface 202 may include a touch screen, pointing device, or any other input devices.

The memory 204 of the provider-patient encounter device 200 may include: a service code (e.g., service code-1 208, and service code-2 210), a service code-1 description 212, a context sponsor (CS) name 214, a CS service code name 216 (e.g., name of a product, service, and information offered by the context sponsor), and CS service code content 218 (e.g., description of the product, service, and information offered by the context sponsor), a supplemental service code (SSC) content request 220, and a SSC content delivery method 222 indicator. The service code (e.g., service code-1 208) may represent a provider demographic code (e.g., a medical specialty), a medical procedure code or a medical diagnosis code, and include: a service priority code-1 224, and a supplemental service code-1 226. Service code-1 208 may indicate the type of context sponsor content LynxIT server 102 may assign to service code-1 208, further indicated by the service code-1 description 212. In one implementation, LynxIT server 102 sets the service priority code-1 224 and service priority code-2 228 to define the order in which the provide-patient encounter device 200 presents corresponding service code-1 208 and service code-2 210 to provider 110 Supplemental service code-1 226 and supplemental service code-2 230 may represent additional content assigned to service code-1 208 and service code-2 210, respectively. For example, provider 110 may select a service code-1 208 that causes the provider-patient encounter device 200 to present content assigned to service code-1 208, and the content may present an option to provider 110 to view, and receive additional information assigned to supplemental service code-1 226. In one implementation, the LynxIT server 102 may assign service code-1 208 to context sponsor-1 104 and supplemental service code-1 226 to context sponsor-2 106 so that different context sponsors provide content to the service code and supplemental service code set. The LynxIT server 102 may automatically maintain, and deliver a complete list of service codes representing medical diagnosis and medical procedures.

The context sponsor (CS) name 214 may indicate the name of a context sponsor assigned to a service code or content specified by the context sponsor-1 104. The CS service code name 216 may represent a description of a product, a service, or information specified by the context sponsor-1 104 that the provider-patient encounter device 200 presents when provider 110 selects the corresponding service code. In one implementation, the CS service code content 218 represents the content presented to provider 110 when provider 110 selects service code-1 208. For example, provider 110 may select a service code-1 208 that causes the provider-patient encounter device 200 to present CS service code content 218 assigned to service code-1 208, and the CS service code content 218 may present a supplemental service code (SSC) content request 220 option to provider 110 that provider 110 may select to view, and receive additional information assigned to supplemental service code-1 226. In one implementation, context sponsor-1 104 receives contact information for provider 110 from LynxIT server 102 when provider 110 selects the service code assigned to the context sponsor-1 104 so that context sponsor-1 104 may contact provider 110 directly. In another implementation, context sponsor-1 104 receives contact information for provider 110 when provider 110 requests additional information regarding a service code assigned to the context sponsor-1 104. Provider 110 may use a SSC content delivery method 222 indicator to specify how provider 110 intends to deliver the additional information to patient 112, which will be further discussed below. In one implementation, provider 110 may use the SSC content delivery method 222 indicator to specify the preferred method the LynxIT service 102 may use to deliver the additional information to provider 110.

The memory 204, shown in FIG. 2, may also include a provider ID 232 identifying provider 110 logged into the provider-patient encounter device 200, patient ID 234 representing patient 112, date 236 and time 238 of a provider-patient encounter, a calendar 240 and contacts 242 for provider 110, and a provider GEO sensitivity 244. The provider GEO sensitivity 244 (e.g., state, region or global code, zip code and radius designation) may indicate the context sponsors (e.g., context sponsor-1 104, context sponsor-2 106, and context sponsor-3 108) assigned to deliver CS service code content 218, and supplemental service code content 246 to provider 110. In other words, the LynxIT server 102 may assign context sponsors to specific geographical regions. The memory 204 may further include user interaction logic 248, and billing generation logic 250 executed by the processor 206. In one implementation, the user interaction logic 248 controls inputs to the provide-patient encounter device 200 from provider 110, and receipt of CS service code content 218 and supplemental service code content 246 by provider 110. The billing generation logic 250 may operate to produce billing information 252 from patient information 254 retrieved from an external storage 256 device, and information stored on the provide-patient encounter device 200. In one implementation, provider 110 receives patient information 254 from various sources, and stores the patient information 254 on the external storage 256 device. The provider-patient encounter device 200 may enable provider 110 to create, edit, and delete patient information 254.

FIG. 2 also shows a provider controlled information delivery system 258 that provider 110 may use to deliver CS service code content 218, and supplemental service code content 246 to patient 112 and to provider 110. The provider controlled information delivery system 258 may include various components necessary to deliver CS service code text content 260, CS service code video content 262, CS service code audio content 264, and other service code sensory content provided by the context sponsor, or any combination thereof. For example, patient 112 may request that provider 110 deliver the patient 112 educational information (e.g., a newsletter) regarding a medical diagnosis or medical procedure related to treatment for patient 112. Provider 110 may select the SSC content request 220 option assigned to a supplemental service code-1 226 to cause the provider controlled information delivery system 258 to print the newsletter that provider 110 presents to patient 112. In another implementation, the SSC content request 220 option selected by provider 110 may cause the provider controlled information delivery system 258 to initiate an email transfer or a multimedia presentation for patient 112 to view. In one implementation, the provider-patient encounter device 200 may use a provider demographics 268 indicator (e.g., indicates the medical specialties of provider 110) to determine the context sponsor content (e.g., the context sponsor (CS) name 214, CS service code name 216, and CS service code content 218, and supplemental service code content 246) to present to provider 110. In another implementation, the provider-patient encounter device 200 may deliver information to the provider controlled information delivery system 258 to enable provider 110 to generate a prescription order for patient 112, and electronically deliver the prescription to an order fulfillment location (e.g., pharmacist).

Figure 3:
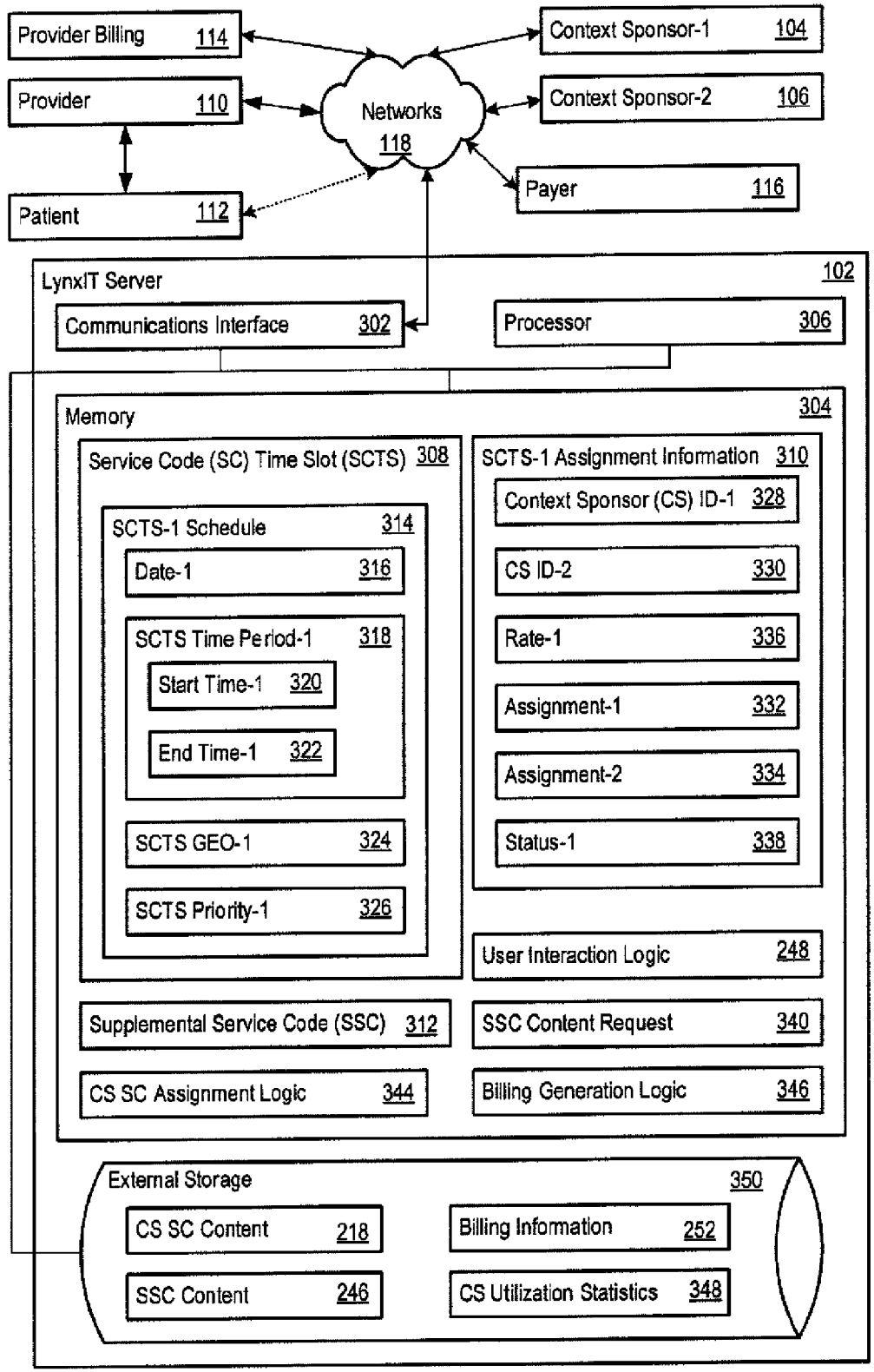
FIG. 3 illustrates the LynxIT Server.

FIG. 3 illustrates the LynxIT server 102. The LynxIT server 102 may include a communications interface 302, a memory 304, and processor 306. In one implementation, the communications interface 302 may enable the exchange of information between various components of the LynxIT system configuration 100 through the network 118 (e.g., the "Internet"), including: context sponsors (e.g., context sponsor-1 104, and context sponsor-2 106), provider 110, patient 112, and provider billing 114. The memory 304 may include a service code time slot (SCTS) 308, a SCTS assignment information 310, and a supplemental service code 312.

The service code time slot (SCTS) 308 may identify a SCTS-1 schedule 314 for service code-1 208 that includes a date-1 316 indicator and SCTS time period-1 318 indicator. For example, when provider 110 selects service code-1 208 from the provider-patient encounter device 200 on the date and time indicated by date 236 and time 238, the SCTS 308 may identify the context sponsor (CS) name 214, CS service code name 216, and CS service code content 218 assigned to context sponsor-1 104 to present to provider 110. The SCTS time period-1 318 may include a start time-1 320 and an end time-1 322 assigned to the SCTS-1 schedule 314 so that the LynxIT server may provide multiple SCTS 308 time slots for service code-1 208 to multiple context sponsors (e.g., context sponsor-1 104, context sponsor-2 106, and context sponsor-3 108). The SCTS-1 schedule 314 may further include a SCTS GEO-1 324 to indicate whether LynxIT server 102 has assigned context sponsor CS service code content 218, and supplemental service code content 246 to a geographical region assigned to the SCTS-1 schedule 314. In one implementation, SCTS GEO-1 324 may correspond to a geographical region that a context sponsor desires to focus advertising, and the GEO sensitivity 244 indicates whether to deliver CS service code content 218, and supplemental service code content 246 to provider 110 in a specific geographical region when provider 110 selects service code-1 208. The SCTS-1 schedule 314 may further include a SCTS priority-i 326 that indicates the priority of the SCTS-1 schedule 314. For example, the LynxIT server 102 may assign context sponsor-1 104 and context sponsor-2 106 the same service code-1 208 for the same time period (e.g., the Monday of every week from 10:00 a.m. to 12:00 p.m. between the beginning of January and the end of March) with different SCTS priority-1 326 values for the service code time slots assigned to context sponsor-1 104 and context sponsor-2 106, respectively, causing the provider-patient encounter device to present content (e.g., context sponsor (CS) name 214, CS service code name 216, CS service code content 218, and supplemental service code content 246) from context sponsor-1 104 and context sponsor-2 106 in a LynxIT server administrator specified order.

The SCTS-1 assignment information 310 includes context sponsor identifiers (e.g., CS ID-1 328, and CS ID-2 330) that indicate the context sponsors (e.g., context sponsor-1 104, and context sponsor-2 106) and their corresponding assignments (e.g., assignment-1 332 and assignment-2 334) for a particular service code time slot (SCTS) 308. The SCTS-1 assignment information 310 may further indicate a status-1 338 of SCTS 308 (e.g., available, assigned, and reserved). Similarly, the LynxIT administrator may assign a supplemental service code (SSC) 312 for a service code time slot to a context sponsor, as described above for service code-1 208.

The memory 304 may further include a SSC content request 340 received from provider 110 that causes LynxIT server 102 to coordinate delivery of supplemental service code content 246 to provider 110 from a context sponsor (e.g., context sponsor-2 106). The memory 304 may also include user interaction logic 248, context sponsor (CS) service code (SC) assignment logic 344, and billing generation logic 346 that processor 306 executes.

In one implementation, the user interaction logic 248 may enable the LynxIT administrator to view available service code time slots 308, and assign (e.g., assignment-1 332 and assignment-2 334) for service code time slots 308 for service code-1 208, service code-2 210, and supplemental service codes 312. The user interaction logic 248 may enable context sponsors to submit content (e.g., the context sponsor (CS) name 214, CS service code name 216, and CS service code content 218 and supplemental service code content 246) to the LynxIT server 102 for review and approval by a LynxIT administrator. In one implementation, the user interaction logic 248 may operate to collect and report context sponsor utilization statistics 348 to users authorized by the LynxIT server 102. For example, each occurrence of provider-patient encounter device 200 presenting CS service code content 218, and supplemental service code content 246 to provider 110 may cause provider-patient encounter device 200, and LynxIT server 102 to collect context sponsor utilization statistics 348. In one implementation, the LynxIT server 102 uses the context sponsor utilization statistics 348 to inform context sponsor-1 104 regarding the effectiveness of SCTS 308 SCTS-1 schedule 314. The user interaction logic 248 may produce summary reports for provider 110 to review that show a list of content sponsors (e.g., context sponsor-1 104, context sponsor-2 106, and context sponsor-3 108) the provider 110 has selected and/or viewed during a particular period (e.g., the beginning and/or end of a day, beginning and/or end of a charge capture session, at the time of a synchronization with the LynxIT server 102, and/or on demand) so that provider 110 can conduct follow up review and research of context sponsor content (e.g., CS service code content 218 and supplemental service code content 246).

The context sponsor service code assignment logic 344 may use the context sponsor utilization statistics 348 to evaluate the rate-1 336 for SCTS 308, and operate to analyze the merit of assignments (e.g., assignments-1 332 and assignments-2 334) to context sponsors (e.g., context sponsor-1 104 and context sponsor-1 106) to determine which context sponsor to assign SCTS 308 SCTS-1 schedule 314. The context sponsor service code assignment logic 344 may further operate to change the status of SCTS-1 assignment information 310 status-1 338 (e.g., available, reserved, and assigned). The billing generation logic 346 may operate to retrieve, produce and store billing information 252 on external storage 350.

Figure 4:
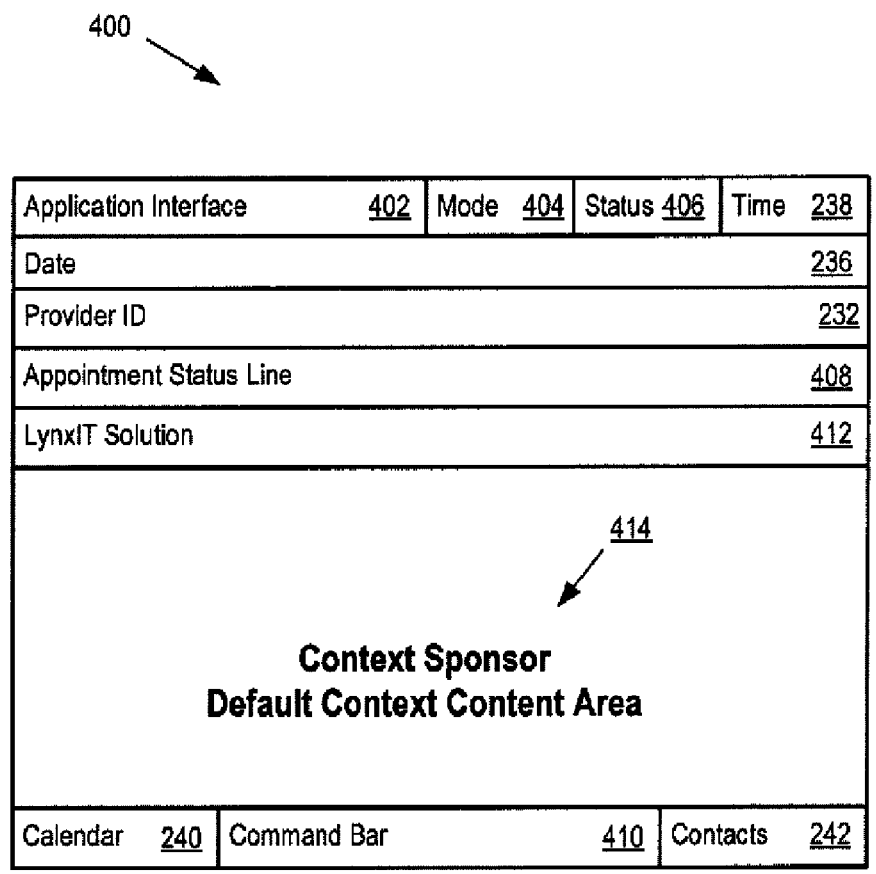
FIG. 4 shows a provider-patient encounter device default interface.

FIG. 4 shows a provider-patient encounter device default interface 400. The provider-patient encounter device default interface 400 (e.g., welcome screen) may include an application interface 402 that indicates the name of the application user interface currently presented to provider 110, and mode 404 and status 406 indicators of the application. The provider-patient encounter device default interface 400 may use animated icons to indicate the mode and status (e.g., an audio-on, data transfer, and working). The provider-patient encounter device default interface 400 may include an appointment status line 408 that presents a list of pending provider 110 appointments to provider 110, LynxIT Solution 412 indicator that indicates the source of the application user interface presented to provider 110, as well as the provider ID 232, date 236, time 238, and calendar 240 and contact 242 options. The provider-patient encounter device default interface 400 may include a command bar 410 that presents various available commands to provider 110, and enable provider 110 to view and select additional commands (e.g., keyboard, scroll bar, save, and delete option).

The provider-patient encounter device default interface 400, illustrated in FIG. 4, also may include a context sponsor default context content area 414. In one implementation, the context sponsor default context content area 414 may present different context sponsor names 214 based on a schedule defined by SCTS-1 schedule 314 assigned to context sponsor-1 104 identified by ID-1 328. In one implementation, the LynxIT server 102 may designate a default service code, and SCTS-1 schedule 314 that direct the provider-patient encounter device 200 to present context sponsor-1 104 context sponsor (CS) name 214, CS service code name 216 (e.g., name of the product, service, and information offered by the context sponsor), and CS service code content 218 (e.g., description of the product, service, and information offered by the context sponsor) in the context sponsor default context content area 414 without requiring provider 110 to select service code-1 208 assigned to context sponsor-1 104. In other words, the LynxIT server may assign a default context (e.g., default service code and SCTS schedule) to a context sponsor ID to enable additional opportunities to present context sponsor content to provider 110 without requiring provider 110 to select a particular service code.

Figure 5:
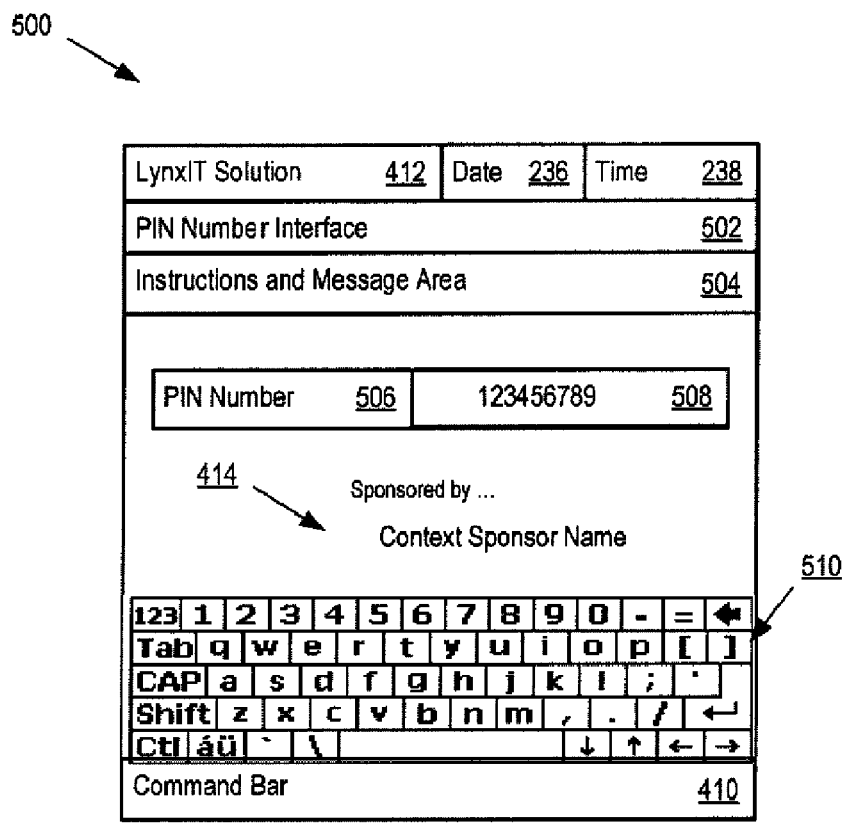
FIG. 5 shows a PIN number entry interface.

FIG. 5 shows a PIN number entry interface 500 of the provider-patient encounter device 200. The PIN number entry interface 500 may present a PIN number interface 502 to further describe the interface to provider 110, an instructions and message area 504, and a PIN number 506 entry area for provider 110 to input their PIN number 508 using a keyboard 510. The provider-patient encounter device 200 may implement the keyboard 510 as a physical keyboard or touchscreen virtual keyboard. The PIN number entry interface 500 further includes a context sponsor default context content area 414 that allows context sponsors (e.g., context sponsor-1 104 and context sponsor-2 106) additional opportunities to present context sponsor content (e.g., the context sponsor (CS) name 214, CS service code name 216, CS service code content 218, and supplemental service code content 246) to provider 110 without requiring provider 110 to select a particular service code.

FIG. 6 shows a service code selector interface 600 that the provider-patient encounter device 200 may present to provider 110 so that the provider may select service codes (e.g., service codes 604-612) to identify medical diagnosis and medical procedures used to deliver healthcare to patient 112 indicated by patient ID 234. The provider-patient encounter device 200 may present the service code selector 602 interface indicator to inform provider 110 when provider 110 and provider-patient encounter device 200 enable the service code selector interface 600. In one implementation, the service code selector interface 600 may present a list of service codes (e.g., service codes 604-612) that provider 110 may view using a navigation aid 614, and add 616 (e.g., assign) and delete 618 (un-assign) to patient ID 234. In one implementation, if provider 110 selects service code-2 606 the service code selector interface 600 presents service code-2 description 620 (e.g., the service code may represent a medical diagnosis "intrinsic asthma unspecified"), and the provider-patient encounter device 200 may determine, and present to provider 110 the context sponsor (CS)-2 name 622, CS service code name 624, and CS service code content 624 assigned to the SCTS-1 schedule 314 for service code-2 606. The context sponsor (CS)-2 name 622, CS service code name 624, and CS service code content 624 may include supplemental service code (SSC) content request 220 option (e.g., a hyperlink to additional information) that provider 110 may select to view or receive additional information. For example, context sponsor (CS)-2 name 622 may represent a hyperlink that provider 110 may select to view additional information. Although the provider-patient encounter device 200 may present content of various context sponsors as the provider 110 selects multiple service codes during a patient encounter, when the provider 110 indicates a final diagnosis for a patient 112 the provider-patient encounter device 200 may present the content of a particular context sponsor base on the final diagnosis and/or the various service codes selected by the provider 110 during the patient encounter.

Figure 7:
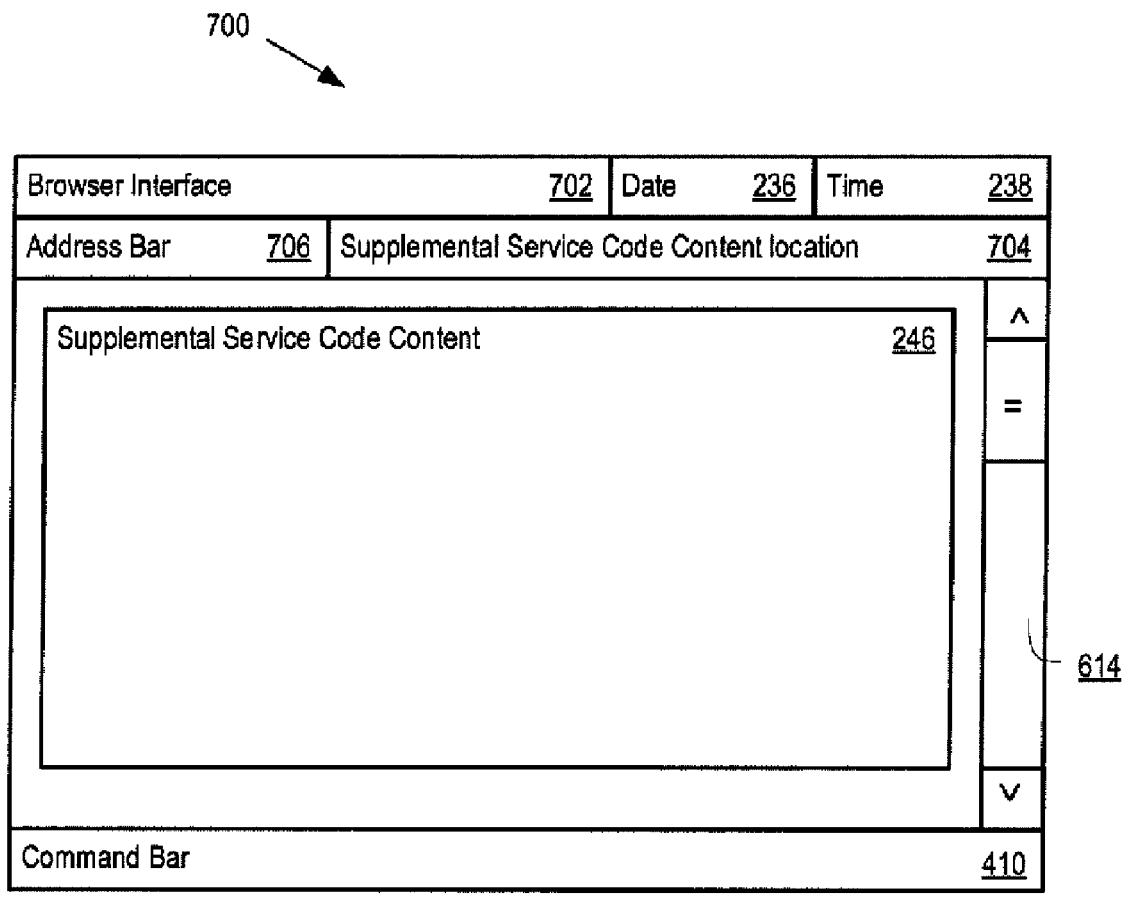
FIG. 7 shows a supplemental service code content interface.

FIG. 7 shows a supplemental service code content interface 700 that the provider-patient encounter device 200 may enable when provider 110 selects supplemental service code (SSC) content request 220 option (e.g., a hyperlink to additional information). In one implementation, the supplemental service code content interface 700 may enable a browser interface 702 that presents supplemental service code (SSC) content 246, and presents the supplemental service code content location 704 in an address bar 706 of the browser interface 702. The supplemental service code (SSC) content 246 may also include supplemental service code (SSC) content request 220 option (e.g., a hyperlink to additional information).

FIG. 8 illustrates a supplemental service code selector interface 800. In one implementation, provider 110 may use the supplemental service code selector interface 800 to indicate the supplemental service code content delivery method 222 preferred, and appropriate for patient 112 identified by patient ID 234 to receive supplemental service code content 246. In one implementation, the provider-patient encounter device 200 may present a supplemental service code selector 802 interface indicator to inform provider 110 when provider 110 and provider-patient encounter device 200 enable the supplemental service code selector interface 800. In another implementation, provider 110 may select from a list of supplemental service codes (e.g., 804-816) particular supplemental service codes (e.g., SSC-4 810 and SSC-6 814) for patient ID 234, and define the appropriate supplemental service code delivery methods 222 to use to deliver the supplemental service code content 246 to patient 112, including a patient physical address 818 method, a provider location 820 method, an electronic messaging to patient 822 method, and a patient voice messaging 824 method. For example, provider 110 may select the provider location 820 supplemental service code delivery method 222 causing the provider controlled information delivery system 258 to present a multimedia presentation to patient 112 in the office of provider 110. In the same example, provider 110 may select the patient physical address 818 supplemental service code delivery method 222 causing the provider controlled information delivery system 258 to initiate mailing printed material to patient 112. The LynxIT server may deliver the supplemental service code content to a provider controlled information delivery system. The provider may deliver the supplemental service code content to the patient using the delivery method established by the patient and provider.

Figure 9:
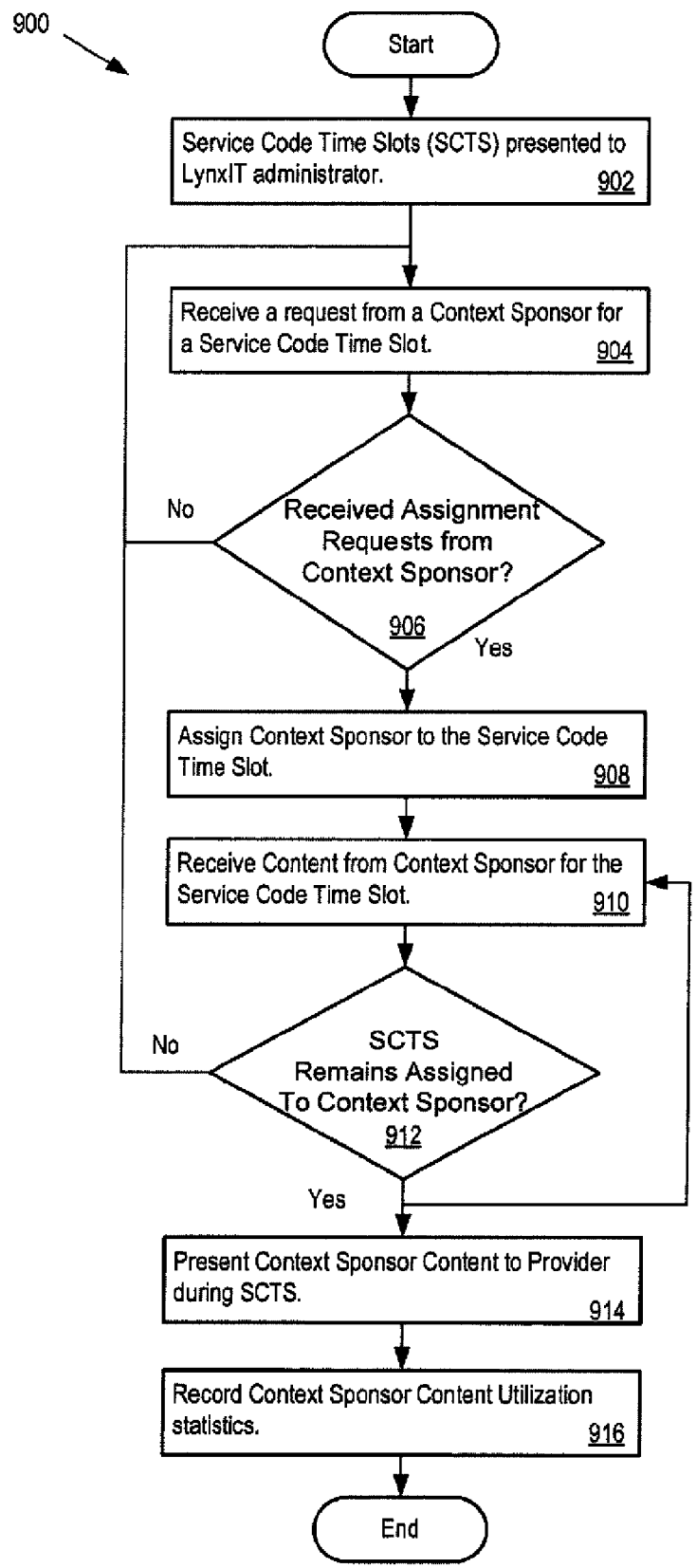
FIG. 9 shows a flow diagram of how the provider-patient encounter application may collect context sponsor content utilization statistics.

FIG. 9 shows a flow diagram of how the provider-patient encounter device 200 may collect context sponsor content utilization statistics 348. The LynxIT server 102 may present service code time slots (e.g. SCTS 308) to the LynxIT administrator (902). The LynxIT server 102 may allow context sponsors to request assignments (e.g., assignment-1 332 and assignment-2 334) for service code time slots. In one implementation, the LynxIT administrator may evaluate requests received from context sponsor-1 104 for SCTS-1 schedule 314 for service code-1 208, service code-2 210, and supplemental service code 312 (904). The LynxIT administrator may continue to review assignment requests for service code time slot SCTS-1 schedule 314 until the LynxIT administrator receives sufficient information to assign a context sponsor a service code time slot (906). The LynxIT server 102 may assign service code time slot SCTS-1 schedule 314 to context sponsor-1 104 for service code-1 208 (908), and enable context sponsor-1 104 to submit content (e.g., the context sponsor (CS) name 214, CS service code name 216, CS service code content 218, and supplemental service code content 246) (910). A LynxIT server 102 administrator may review and approve the content submitted by context sponsor-1 104, and deliver the context sponsor content to the provider-patient encounter device 200. The context sponsor for an assigned service code, and service code time slot may submit content for approval and review to the LynxIT server 102 anytime during the context sponsor assignment to enable the context sponsor to maintain updated content (912). The provider-patient encounter device 200 may present the context sponsor content to provider 110 during the service code time slot (914). The provider-patient encounter device 200 and the LynxIT server 102 may operate to collect and report context sponsor utilization statistics 348 to users authorized by the LynxIT server 102 (916).

In one implementation, the LynxIT server 102 assigns context sponsor-1 104 SCTS-1 schedule 314 for service code-1 208, where the service code-1 208 represents a default service code (e.g., a provider demographic code indicating a medical specialty) that directs the provider-patient encounter device 200 to present context sponsor-1 104 content (e.g., context sponsor (CS) name 214, CS service code name 216, CS service code content 218, and supplemental service code content 246), in the context sponsor default context content area 414, to provider 110 with a matching provider demographic 268, without requiring provider 110 to select the service code-1 208. In the above implementation, the provider-patient encounter device 200 and the LynxIT server 102 may operate to log each occasion when the context sponsor default context content area 414 presents the assigned context sponsor content to provider 110.

In another implementation, the LynxIT server 102 assigns context sponsor-2 106 SCTS-1 schedule 314 for service code-2 210, where service code-2 210 represents a medical diagnosis code that directs the provider-patient encounter device 200 to present context sponsor-2 106 content (e.g., context sponsor (CS) name 214, CS service code name 216, CS service code content 218, and supplemental service code content 246) to provider 110 when provider 110 selects service code-2 210. In the above example, the provider-patient encounter device 200 and the LynxIT server 102 may operate to log each occasion when provider 110 selects service code-2 210, and provider-patient encounter device 200 presents context sponsor-2 106 content to provider 110. Similarly, the provider-patient encounter device 200 and the LynxIT server 102 may operate to log each occasion when provider 110 selects supplemental service code content 246.

Figure 10:
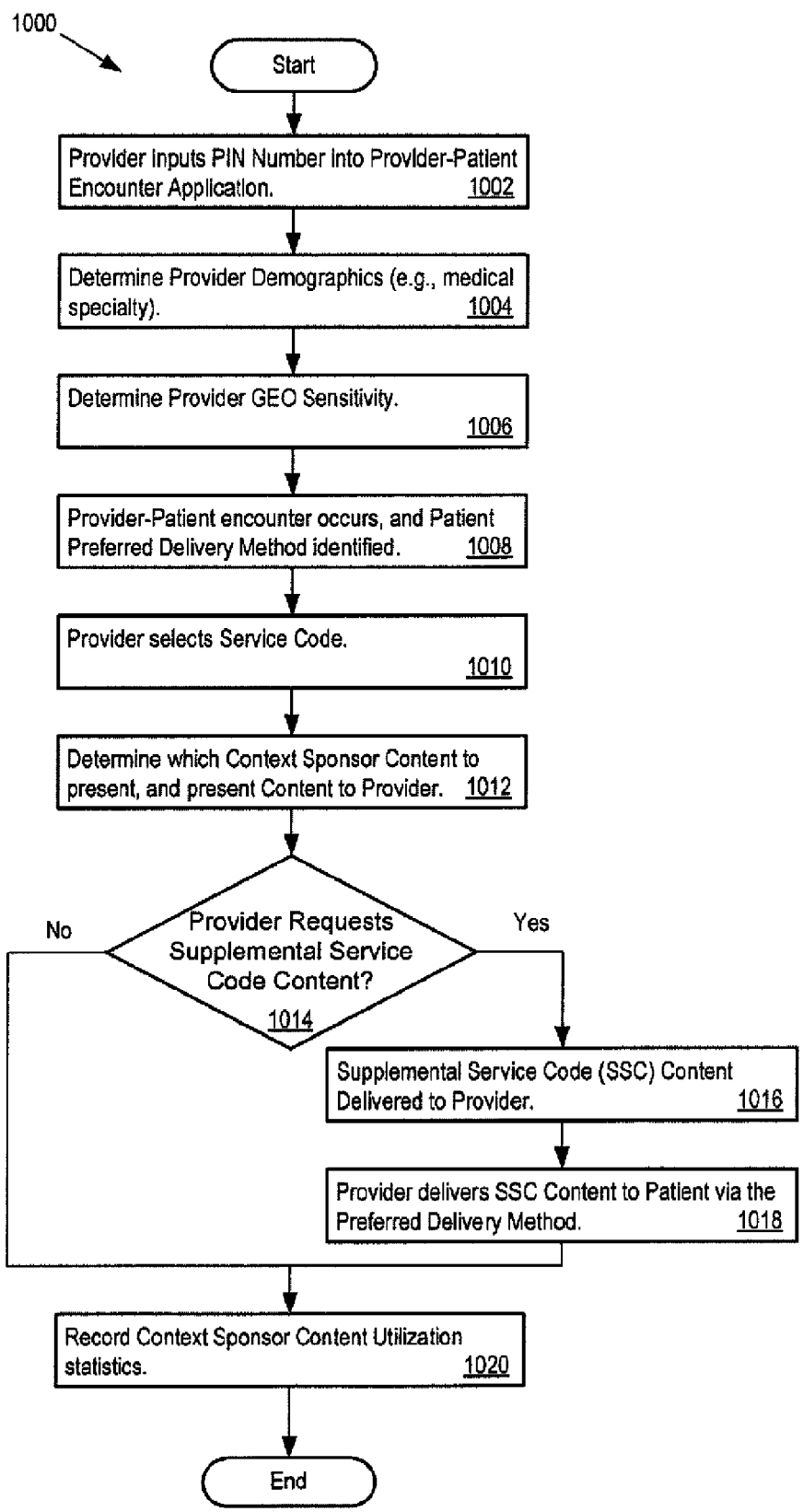
FIG. 10 shows a flow diagram of how providers deliver supplemental service code content to patients.

FIG. 10 shows a flow diagram of how providers 110 may deliver supplemental service code content 246 to patients 112. Provider 110 may enter their PIN number 508 into the provider-patient encounter device 200 PIN number entry interface 500 (1002). The provider-patient encounter device 200 may determine the provider demographics 268 based on information from other sources (e.g., a provider registry) (1004). The provider-patient encounter device 200 may identify the geographical location of a provider 110 (e.g., a state, region or global code, zip code and radius designation) and use the GEO sensitivity 244 to identify which context sponsor content to present to the provider 110 (1006). During the provider 110 consultation with patient 112, the provider 110 may establish and confirm the supplemental service code content delivery method 222 with patient 112 (1008). In one implementation, provider 110 may also select a service code-1 208 in the course of the consultation with patient 112 (1010). The provider-patient encounter device 200 may determine the context sponsor content (e.g., CS service code content 218 and supplemental service code content 246) to present to provider 110 based on the service code selected by provider 110 (1012). In the event provider 110 selects supplemental service code (SSC) content request 220 option assigned to supplemental service code-1 226 (1014), the LynxIT server may present supplemental service code content 246 to provider 110 via the provider-patient encounter device 200, and deliver the supplemental service code content 246 to the provider controlled information delivery system 258 (1016). Provider 110 may deliver the supplemental service code content 246 to patient 112 using the SSC content delivery method 222 indicator (1018). The provider-patient encounter device 200 and the LynxIT server 102 may operate to log each occasion when provider 110 selects supplemental service code content 246 to record context sponsor content utilization statistics (1020).

FIG. 11 illustrates a service code time slot (SCTS) schedule location 1100. In one implementation, the LynxIT server 102 may enable the LynxIT administrator to use a browser interface 1102 to visit a SCTS—schedule location 1104 to enter a service code (e.g., service code-7 1108) and view the corresponding SCTS schedules (e.g., 1110-1116). The LynxIT system configuration 100 and LynxIT server 102 may limit viewing of service code schedules to authorized users including context sponsors, and may require security access (e.g., a login) to gain access to the location. The service code time slot (SCTS) schedule location 1100 may enable context sponsors to quickly identify service codes (e.g., using a pull-down list 1118) and determine preferred SCTS schedules. In one implementation, the service code time slot (SCTS) schedule location 1104 may also include SCTS utilization statistics 1120 that report utilization statistics for a service code (e.g., service code-7 1108) and SCTS schedule (e.g., 1110-1116) based on CS utilization statistics collected for context sponsor assigned service codes and unassigned service codes. Similarly, the LynxIT server 102 may also enable context sponsors to view SCTS schedules for supplemental service codes 312, as described above.

FIG. 12 illustrates a service code time slot (SCTS) context sponsor (CS) assignment site 1200. The LynxIT system configuration 100 and LynxIT server 102 may limit access to the service code time slot (SCTS) context sponsor (CS) assignment site 1200 to authorized users including context sponsors (e.g., context sponsor-1 104) identified by a context sponsor ID (e.g., CS ID-1 328), and may require security access (e.g., a login) to gain access to the location. In one implementation, the LynxIT server 102 may enable the LynxIT administrator to manage content for a context sponsor-1 104 identified by CS ID-1 328, using a browser interface 1102 to enter assignment (e.g., 1204-1212) for SCTS schedules (e.g., 1214-1222) for a service code (e.g., service code-5 1224) at the service code time slot—context sponsor assignments location 1202. The LynxIT administrator may use commands to clear 1226 an assignment that has not been submitted, and submit 1228 an assignment. The LynxIT server 102 may present an assignment status-1 1230 and an assignment rank-1 1232 to the LynxIT administrator for a context sponsor (e.g., context sponsor-1 104). The assignment status-1 1230 may indicate a pending, accepted, and rejected status. The assignment rank-1 1232 may indicate the ranking of assignment-1 1204 in relation to other assignments for the same service code SCTS-1 schedule 1214, and other quality factor rating (e.g., SCTS utilization statistics 1120 value analysis). Similarly, the LynxIT server 102 may also enable the LynxIT administrator to assign to context sponsors SCTS schedules for supplemental service codes 312, as described above.

FIG. 13 illustrates a context sponsor content management site 1300. The LynxIT server 102 may enable the LynxIT administrator to manage content from a context sponsor (e.g., context sponsor-1 104) identified by a context sponsor ID (e.g., CS ID-1 328) assigned a service code, and/or supplemental service code (e.g., service code-5 1302). The LynxIT administrator may manage context sponsor content (e.g., CS service code text content 260, CS service code video content 262, CS service code audio content 264, and CS service code other sensory content 1306) using a context sponsor content management location 1304. In one implementation, the LynxIT server 102 may enable a context sponsor (e.g., context sponsor-1 104) identified (e.g., CS ID-1 328) to input content. In another implementation, the context sponsor content management location 1304 may enable the LynxIT administrator to maintain updated content for assigned service codes, and assigned supplemental service codes for context sponsor-1 104.

FIG. 14 illustrates a service code link interface 1400 that the provider-patient encounter device 200 may present to provider 110 to capture a provider-patient encounter. In one implementation, provider 110 may use the service code link interface 1400 to define relationships between service codes (e.g., 1402-1412) to capture a provider-patient encounter (e.g., medical diagnosis and medical procedures related to the treatment of patient 112 identified by patient ID 234). For example, provider 110 may select service code-2 1402 for patient 112 identified by patient ID 234, and the provider-patient encounter device 200 may indicate the service code type-2 1414 (e.g., medical procedure). Provider 110 may create a relationship between the service code indicated by the service code link 1416 (e.g., service code-2 1402) and a service code (e.g., service code-9 1410) by adding the service code (e.g., service code-9) from a list of available SC 1416 to a list of linked SC 1418 (e.g., indicated by the arrow 1422). In one implementation, provider 110 may also delete service codes from linked SC 1420. In one implementation, the service code link interface 1400 may present a service code-9 description for service code-9 selected from either available SC 1418 or linked SC 1420 (e.g., 1404 and 1406).

FIG. 15 illustrates a provider-patient encounter device 200 patient profile interface 1500. The patient profile interface 1500 enables provider 110 to create, edit, and delete patient information 254 for patient 112 identified by patient ID 234. The provider-patient encounter device 200 may present the patient profile interface indicator 1502 to inform provider 110 when provider 110 and the provider-patient encounter device 200 enables the patient profile interface 1500. Provider 110 may use the patient profile interface 1500 to select a default supplemental service code content (SSC) delivery method 1506 that provider 110 may use when provider 110 does not indicate supplemental service code content (SSC) delivery method 222 for specific supplemental service code content 246 using the supplemental service code selector interface 800.

Figure 16:
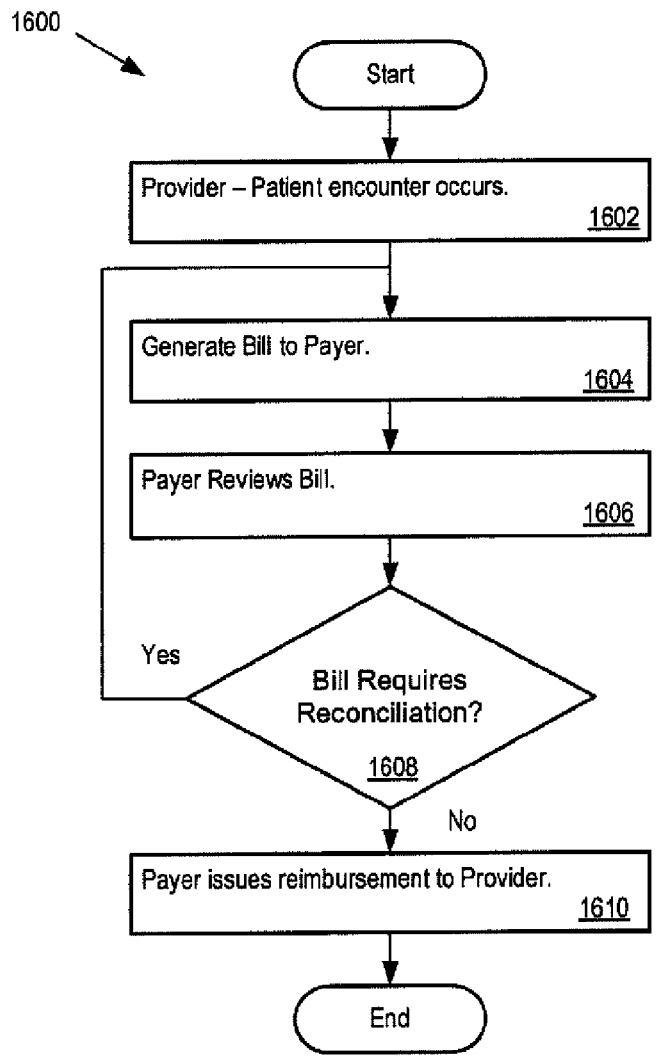
FIG. 16 shows a flow diagram of the revenue cycle for a provider.

FIG. 16 shows a flow diagram of a provider revenue cycle 1600. The LynxIT system configuration 100 may include functionality designed to improve the provider revenue cycle 1600. Generally, the provider revenue cycle 200 may commence with a provider-patient encounter (1602), for example, where provider 110 consults with patient 112 so that provider 110 can diagnose the condition of patient 112. Following the provider-patient encounter, provider 110 may generate a charge that provider billing-1 114 use to produce a bill provider billing-1 114 forwards to payer 116 (1604). Payer 116 may review the bill (1606). Payer 116 may determine whether the bill meets certain criteria before reimbursing provider 110

(1608), and payer 116 may require provider 110 to revise the bill. The payer 116 issues the reimbursement to provider 110, in the event the payer 116 determines that payer 116 requires no revisions to the bill (1610). LynxIT system configuration 100 enables providers 110 to improve the revenue cycle of providers 110, and allows context sponsors to realize opportunities to present their products, services and information to providers 110 efficiently and in a timely manner.

The LynxIT system configuration may include a provider-patient encounter device (e.g., a handheld device) that delivers electronic charge capture to providers, and enables advertisers to present their products and services to providers effectively and economically. The provider-patient encounter device may combine electronic technology and physician designed menu-driven software to enable providers to easily access patient information instantly from anywhere, accurately and quickly select medical diagnosis and procedure codes, link medical diagnoses with procedure codes, and generate and analyze charges. In one implementation, the provider-patient encounter device eliminates the need for billing departments to decipher physician handwriting and store physical files, and enables providers to perform daily and automatic storage of billing information, improves reimbursement rates, and reduces reimbursement cycles. The provider-patient encounter device electronically generated charges may reduce claim preparation time, and first time rejections well below paper based manual charge capture methods, and enable provider billing departments to review and download charges using web based tools. The provider-patient encounter device may further enable providers to view patient information in real-time, as well as products and services available to deliver quality healthcare to patients. The provider-patient encounter device may enable providers to spend more time with their patients while maximizing reimbursements for services provided, and avoid the time wasted resulting from manual charge capture methods.

The provider-patient encounter device may enable healthcare advertisers (e.g., context sponsors) to present their products and services to providers regarding medical products and services, related to medical diagnosis and procedures selected by providers during provider-patient encounters. The LynxIT system configuration may generate revenue from advertisers advertising their products and services to providers using the provider-patient encounter device, and may subsidize the cost to providers using the provider-patient encounter device. The LynxIT system configuration uses the term "context sponsors" to represent advertisers, because the provider-patient encounter device presents products, services and information to providers from advertisers based on context (e.g., a default context such as a welcome screen, and specific context such as a selected medical diagnosis or procedure). The provider-patient encounter device may collect utilization statistics when the provider-patient encounter device presents information from advertisers, or a provider selects or requests information from an advertiser so that advertisers may measure the effective reach of their advertising investment. The provider-patient encounter device may also enable providers to deliver healthcare information to patients using a provider controlled method (e.g., multimedia presentation viewed in the facility of the provider). In one implementation, the LynxIT system configuration allows a LynxIT administrator to assign advertisers to medical diagnosis and procedures (e.g., service codes), and time periods (e.g., service code time slots with various granularity) that the advertisers desire to present their products and services to providers using the provider-patient encounter device. The time periods may be assigned in increments of minutes, hours, and days.

The LynxIT system may offer a full service application service provider (ASP) model so that providers do not have to maintain large and expensive systems at their facilities. The LynxIT system configuration may also enable real-time provider billing and summary information and reporting capabilities. In one implementation, the LynxIT system configuration enables advertisers to realize utilization statistics, and key metrics reporting. In another implementation, the LynxIT system can be implemented to include and/or interface with an electronic medical records system (EMR).

A provider-patient encounter device solves the technical problem of economically and efficiently delivering healthcare information, products and services to providers and patients. The provider-patient encounter device enables healthcare advertisers to present timely healthcare information to providers, and assist providers to deliver the greatest quality of healthcare to patients. The provider-patient encounter device enables advertisers to easily and promptly deliver healthcare advertising, and receive reporting utilization statistics for content presented, selected or requested by a provider.

A number of implementations have been described. Nevertheless, it will be understood that various modifications may be made without departing from the spirit and scope of the invention. Accordingly, other implementations are within the scope of the following claims.

What is claimed is:

1. A method for delivering medical information and services, comprising:
    receiving with a computer to link medical records and advertising content from a plurality of context sponsors, the context sponsors comprising a first context sponsor and a second context sponsor;
    linking, with said computer, content from the plurality of context sponsors to a plurality of service codes, the plurality of service codes comprising a first service code and a second service code, the plurality of service codes representing a medical procedure code or a medical diagnosis code comprising: a provider demographic code, a service priority code, and a supplemental service code;
    presenting the plurality of service codes in a service code selectable list comprising the first service-code and the second service code;
    presenting content from one of the plurality of context sponsors assigned to one of the plurality of service codes when the provider selects one of the plurality of service codes from the plurality of service codes in the service code selectable list.

2. The method of claim 1, wherein the content from the plurality of context sponsors comprises a description of a product and a description of service.

3. The method of claim 1, further comprising:
    defining, via a computer, at least one relationship between the at least one of the plurality of service codes representing a medical diagnosis code and at least one of the plurality of service codes representing a medical procedure.

4. The method of claim 1, further comprising:
    analyzing the service codes selected by the provider from the plurality of service codes in the service code selectable list during a patient-encounter to identify the content from one of the plurality of context sponsors to present to the provider.

5. The method of claim 4, wherein at least one of the plurality of service codes represents a medical procedure code and at least two of the plurality of service codes is a medical diagnosis code.

6. The method of claim 1, where forwarding supplemental service code content to the patient by the provider further comprises: the provider receiving supplemental service code content associated with the supplemental service code of the first service code from a third context sponsor; the provider associating the supplemental service code content with a patient; and the provider identifying a preferred method of delivery to the patient.

7. The method of claim 1, further comprising:
requesting a third context sponsor forward a supplemental service code content associated with the supplemental service code of the first service code to the provider; and
forwarding the supplemental service code content to a patient by the provider.

8. A product for delivering medical information and services comprising:
a machine readable medium; and
instructions stored on the machine readable medium comprising:
user interface logic operable to:
receive content from a plurality of context sponsors, the context sponsors comprising a first context sponsor and a second context sponsor;
assign content from the plurality of context sponsors to a plurality of service codes, the plurality of service codes comprising a first service code and a second service code, the plurality of service codes representing a medical procedure code or a medical diagnosis code comprising: a provider demographic code, a service priority code, and a supplemental service code;
present the plurality of service codes in a service code selectable list comprising the first service code and the second service code;
present content from one of the plurality of context sponsors assigned to one of the plurality of service codes when the provider selects one of the plurality of service codes from the plurality of service codes in the service code selectable list;
request a third context sponsor forward a supplemental service code content associated with the supplemental service code of the first service code to the provider; and
forward supplemental service code content to a patient;
generation logic operable to generate billing information based on the first service code selected by the provider.

9. The product of claim 8, wherein the content from the plurality of context sponsors comprises a description of a product and a description of service.

10. The product of claim 8, further comprising:
definition logic operable to define at least one relationship between at least one of the plurality of service codes representing a medical diagnosis code and at least one of the plurality of service codes representing a medical procedure.

11. The product of claim 10, wherein at least one relationship is defined between at least one of the plurality of service codes that represents a medical procedure code and at least two of the plurality of service codes that represent a medical diagnosis code.

12. The product of claim 8, further comprising:
analyzer logic operable to analyze the service codes selected by the provider from the plurality of service codes in the service code selectable list during a patient-encounter to identify the content from one of the plurality of context sponsors to present to the provider.

13. The product of claim 12, wherein at least one of the plurality of service codes represents a medical procedure code and at least two of the plurality of service codes represent a medical diagnosis code.

14. The product of claim 8, where the user interface logic operable to forward supplemental service code content to the patient by the provider is further operable to: receive supplemental service code content associated with the supplemental service code of the first service code from the third context sponsor; associate the supplemental service code content with a patient; and identify a preferred method of delivery to the patient.

15. A system for delivering medical information and services comprising:
a memory comprising:
user interface logic operable to:
present a first service code time slot and a second service code time slot to a first context sponsor and a second context sponsor,
where the first service code time slot and the second service code time slot identify a time period for a first service code and a second service code, respectively,
where the first service code and the second service code represent a medical procedure code or a medical diagnosis code comprising: a provider demographic code, a service priority code, and a supplemental service code;
receive a request from the first context sponsor and the second context sponsor, respectively, for the first service code time slot, or the second service code time period, or both the first service code time slot or the second service code time period;
receive content from the first context sponsor and the second context sponsor associated with the first service code and the second service code, respectively;
present content from the first context sponsor for the first service code to a provider when the provider selects the first service code;
request the third context sponsor forward supplemental service code content associated with the supplemental service code of the first service code to the provider; and
forward supplemental service code content to a patient;
definition logic operable to assign: the first context sponsor the first service code time slot; the second context sponsor the second service code time slot; and a third context sponsor the supplemental service code associated with the first service code;
generation logic operable to generate a charge to a payer based on the first service code selected by the provider;
a provider database; and
a processor coupled to the memory and the database and operable to execute the user interface logic, definition logic and generation logic.

16. The system of claim 15, where the provider database is controlled by the provider and comprises supplemental service code content associated with the supplemental service code of the first service code.

17. The system of claim 15, where the user interface logic operable to forward supplemental service code content to the patient is further operable to:
   authorize the provider to forward supplemental service code content to the patient; receive supplemental service code content associated with the supplemental service code of the first service code from the third context sponsor; associate the supplemental service code content with a patient; and
   identify a preferred method of delivery to the patient.

18. The system of claim 17, where the preferred method of delivery to the patient comprises: manual delivery to physical address of patient; provider office location; electronic messaging to the patient; and patient voice messaging.

19. The system of claim 15, where the supplemental service code further comprises a supplemental service priority code and a supplemental service code time slot.

20. The system of claim 19, further operable to present a first supplemental service code time slot to the third context sponsor, and receive a request from the third context sponsor for the first supplemental service code time slot.

21. The system of claim 15, where the user interface logic operable to receive content from the first context sponsor is further operable to:
   present a content template for the first context sponsor to input content;
   accept content entered in the content template; and
   receive modifications to the content entered in the content template.

* * * * *

UNITED STATES PATENT AND TRADEMARK OFFICE
CERTIFICATE OF CORRECTION

| | | |
|---|---|---|
| PATENT NO. | : 7,809,590 B2 | |
| APPLICATION NO. | : 11/775603 | |
| DATED | : October 5, 2010 | |
| INVENTOR(S) | : Peter Freebeck et al. | |

It is certified that error appears in the above-identified patent and that said Letters Patent is hereby corrected as shown below:

In column 16, claim 1, line 33, after "with a computer" insert --configured--.

Signed and Sealed this
Twelfth Day of April, 2011

David J. Kappos
*Director of the United States Patent and Trademark Office*